United States Patent [19]

Richards et al.

[11] Patent Number: 5,206,355
[45] Date of Patent: Apr. 27, 1993

[54] PREPARATION OF TRISACCHARIDES (KESTOSES) AND POLYMERS BY PYROLYSIS OF AMORPHOUS SUCROSE

[75] Inventors: Geoffrey N. Richards; Merilyn Manley-Harris, both of Missoula, Mont.

[73] Assignee: The University of Montana, Missoula, Mont.

[21] Appl. No.: 855,355

[22] Filed: Mar. 19, 1992

Related U.S. Application Data

[63] Continuation-in-part of Ser. No. 767,324, Sep. 30, 1991, abandoned.

[51] Int. Cl.$^5$ .................... C07H 1/00; C08B 37/00
[52] U.S. Cl. ............... 536/4.1; 127/DIG. 1; 536/18.5; 536/124; 536/126; 424/439; 424/442; 426/650; 514/892
[58] Field of Search ............... 127/DIG. 1; 536/4.1, 536/18.5, 124, 126; 424/442, 439; 514/892; 426/650

[56] References Cited

U.S. PATENT DOCUMENTS

| | | | |
|---|---|---|---|
| 2,387,275 | 10/1945 | Leuck | 536/124 |
| 3,300,474 | 1/1967 | Flodin et al. | 536/124 |
| 3,766,165 | 10/1973 | Rennhard | 536/124 |
| 4,965,354 | 10/1990 | Yanaki et al. | 536/124 |
| 4,975,534 | 12/1990 | Fox et al. | 536/123 |

FOREIGN PATENT DOCUMENTS

2179946A 3/1987 United Kingdom.

OTHER PUBLICATIONS

Poncini et al, Chemical Abstracts, vol. 94, Abstracts 94:121819y, 1981.
Stanek et al, The Oligosaccharides Academic Press, pp. 258-266, 1965.
Bollmann et al, International Sugar Journal, vol 67(797), pp. 143-146, (1965).
Oku et al, Amer. Inst. of Nutr., vol. 114, pp. 1574-1581, 1983.
Lowary et al, Int. Sugar Journal, vol. 90, No. 1077, pp. 164-167, 1988.
O'Donnell et al. Aust. Journal of Chemistry, vol. 25, pp. 407-412, 1972.
Moody et al, Carbohydrate Research, vol. 124, pp. 201-213, 1983.
Moody et al, Carbohydrate Research, vol. 114, pp. 306-310, 1983.
Moody et al, Carbohydrate Research, vol. 111, pp. 23-29, 1982.
Moody et al, Carbohydrate Research, vol. 108, pp. 13-22, 1982.
Moody et al, Carbohydrate Research, vol. 97, pp. 247-255, 1981.
Manley-Harris et al, Carbohydrate Research, vol. 90, pp. 27-40, 1981.
Poncini et al, Carbohydrate Research, vol. 87, pp. 209-217, 1980.
Manley-Harris et al, Aust. Journal of Chemistry, vol. 33, pp. 1041-1047, 1980.
Manley-Harris et al, Carbohydrate Research, vol. 82, pp. 356-361, 1980.
Richards et al, Aust. Journal of Chem., vol. 31, pp. 1825-1832, 1978.
Covacevich al, Proc. of the Queensland Soc. for Sugar Cane Tech., pp. 171-178, 1974.

(List continued on next page.)

*Primary Examiner*—Ronald W. Griffin
*Attorney, Agent, or Firm*—Lowe, Price, LeBlanc & Becker

[57] ABSTRACT

Sucrose is treated with an acid catalyst to form an amorphous sucrose anhydrous melt. Heating of the anhydrous melt at 80°-100° C. forms three known kestoses and the novel products, viz. α-fructosylsucrose anomers of 6-kestose, neokestose, and 1-kestose. Heating of the anhydrous melt at 125°-175° C. produces a fructoglucan sucrose polymer having a molecular weight of about 2,000 to 10,000 Daltons. All of these products are useful as sweeteners, food additives, additives for animal food, and bulking agents.

38 Claims, 6 Drawing Sheets

OTHER PUBLICATIONS

O'Donnell et al, Aust. Jour. of Chem., vol. 26, pp. 2041–2049, 1973.
Richards et al, Proc. of the Queensland Soc. for the Sugar Cane Tech., pp. 229–234, 1974.
Richards et al, The International Sugar Journal, vol. 76, pp. 103–107, 1974.
Richards et al, The International Sugar Journal, vol. 88, No. 1052, pp. 145–148, 1986.
Oku, Nutritional Reviews, vol. 43, No. 5, pp. 155–165, 1985.
Poncini, The International Sugar Journal, vol. 82, No. 979, pp. 332–335, 1980.
Poncini, La Sucrerie Belge, vol. 100, pp. 221–229, 1981.
Bacon, Biochemistry, vol. 73, pp. 507–514, 1959.
Clevenger et al, Journal of the American Coll. of Toxicology, vol. 7, No. 5, pp. 643–662, 1988.
Darbyshire et al, New Phytol., vol. 81, pp. 29–34, 1978.
Edelman et al, Biochem. J., vol. 98, pp. 787–794, 1966.
Fishbein et al, Vet Hum Toxicol, vol. 30(2), pp. 104–107, 1988.
Haq et al, Canadian Journal of Chemistry, vol. 39, No. 6, pp. 1165–1170, 1961.
Hidaka et al, Shokuhnin Kogyo, vol. 31, pp. 52–58, 1988 (with partial English translation).
Hidaka, Agric., Biol. Chem., vol. 52(5), pp. 1181–1187, 1988.
Hidaka et al, Bifidobacteria Microflora, vol. 5(1), pp. 37–50, 1986.
Mitsuoka et al, Department of Biomedical Science, vol. 31, No. 5–6, pp. 427–436, 1987.
Oda et al, Enzyme Microb. Technology, vol. 13, pp. 495–498, 1991.
Park et al, World Journal of Microbiology and Biotechnology, vol. 7, pp. 331–334, 1991.
Saunders, American Association of Cereal Chemists, Inc., vol. 52, pp. 472–479, 1975.
Saunders et al, Cereal Chemistry, vol. 47, pp. 85–92, 1968.
Shiomi et al. Agr. Bio. Chem., vol. 58(4), pp. 548–556, 1978.
Shiomi et al, Agr. Biol. Chem., vol. 40(3), pp. 567–575, 1976.
Stone-Dorshow et al, Am. J. Clin. Nutr., vol. 46, pp. 61–65, 1987.
Tokunaga, J. Nutr. Sci. Vitaminol., vol. 32, pp. 111–121, 1986.
Tokunaga et al, Amer. Inst. of Nutr., pp. 553–559, 1989.
Yamashita et al, Nutrition Research, vol. 4, pp. 961–966, 1984.

PREPARATION OF TRISACCHARIDES (KESTOSES) AND POLYMERS BY PYROLYSIS OF AMORPHOUS SUCROSE

CROSS REFERENCE TO RELATED APPLICATIONS

This application is a continuation-in-part of Ser. No. 07/767,324, filed Sep. 30, 1991, now abandoned.

FIELD OF THE INVENTION

This invention relates to the formation of trisaccharides, other oligosaccharides and polysaccharides, by pyrolysis of sucrose and products produced thereby.

BACKGROUND ART

Prior studies on the thermal degradation of sucrose have indicated the formation of trisaccharides, presumed to be kestoses (fructosylsucrose derivatives). The thermal decomposition of sucrose is known to proceed via scission of the glucosidic linkage to form a resonance-stabilized fructosyl cation which may then be subject to nucleophilic attack by oxygens of alcohols present in the reaction mixture. Such transfructosylations have been studied in detail with simple alcohols. The assumption of kestose formation mentioned above is predicated upon the fact that the hydroxyls of untreated sucrose could also act as nucleophiles. The primary hydroxyls are the most likely to act thus, since earlier studies showed that the fructosyl cation reacts more readily with primary than with secondary alcohols.

Bollmann and Schmidt-Berg, International Sugar Journal, Vol. 67,(797), p. 143-146, (1965), heated dry crystalline sucrose at 170° C. and identified, by paper chromatography, thirteen products of which five were non-reducing trisaccharides; one of these being identified as 6-kestose. Most of the literature references to kestoses pertain to their biological origins. These trisaccharides, together with their higher d.p. homologues, are found in a number of flowering plant families, where they constitute precursors of the fructan storage polymers and have been implicated in frosthardiness and osmotic control.

There has also been some recent interest in the enzymic preparation from sucrose of 1-kestose and its higher homologues which are reported to have potential as non-nutritive sweeteners, T. Oku, et al "*J. Nutr.*, 114 (1984), p. 1574-1581; S. C. Ziesenitz et al "Proc. Ann. Meeting, Amer. Inst. Nutr. in *J. Nutr.*, 117, (1987), p. 846-851, and H. Hidaka et al, published United Kingdom patent application No. 2,179,946A, (1987).

Lowary et al, *Int. Sugar Journal*, 1988, Volume 90, No. 1077, pages 164-167, disclose the thermal degradation of non-crystalline sucrose (sucrose melts). There are also disclosed methods to produce amorphous sucrose by dissolving crystalline sucrose in minimal water and then evaporating the water to form an amorphous sucrose melt.

There has also been substantial work involving the polymerization of various sugars such as dextrose to produce various types of products. Thus, U.S. Pat. No. 2,387,375 discloses the polymerization of certain sugars to produce heterogenous mixtures of polymers having a wide variation in degree of polymerization. The polymerization is conducted in the presence of a catalyst or combination of catalysts, such as metaboric acid. Also, U.S. Pat. No. 3,766,165 discloses the polycondensation of saccharides in the presence of polycarboxylic acid catalysts at reduced pressure. In this patent, glucose or maltose is subjected to anhydrous melt polymerization using an edible acid such as citric acid as a catalyst and cross-linking agent. U.S. Pat. Nos. 4,975,534 and 4,965,354 disclose thermal reactions of a sugar such as glucose with glutamic acid and hydrogen chloride respectively, and U.S. Pat. No. 3,300,474 discloses the formation of sucrose ether copolymerizates by reaction of sucrose in aqueous solution in the presence of an alkaline catalyst.

To Applicants' knowledge, however, the present invention provides for the first time a process for the formation of new trisaccharides (iso-kestoses) by heating acid sucrose melts, and also provides novel fructoglucan polymers resulting from the polymerization of amorphous sucrose.

SUMMARY OF THE INVENTION

It is accordingly one object of the invention to provide novel products resulting from amorphous sucrose thermolysis and processes of production of such products.

A further object of the invention is to provide novel iso-kestose products and derivatives thereof and methods for their production by thermolysis of amorphous sucrose.

A still further object of the invention is to provide a method for the thermolysis of amorphous sucrose in the presence of an acid catalyst to produce novel fructoglucan polymers and products produced from the method.

An even further object of the invention is to provide food compositions containing the novel products of the invention.

Other objects and advantages of the invention will become apparent as the description thereof proceeds.

In satisfaction of the foregoing and other objects and advantages, there are provided by the present invention the novel products, iso-6-kestose (an α-fructosylsucrose anomer of 6-kestose), iso-neokestose, and iso-1-kestose (α-fructosylsucrose anomers of neo- and 1-kestoses, respectively), and a reducing disaccharide containing fructose and glucose, (6-[α-D-fructofuranosyl]-D-glucose). Methods for preparation of these products comprise the thermolysis of amorphous sucrose under special conditions, e.g., reaction temperatures of 80°-110° C., and isolation of the products. Important features of the process are that the sucrose be substantially or fully amorphous (noncrystalline), a small amount of an acid catalyst be used, e.g., citric acid, tartaric acid, or phosphoric acid, and the amorphous sucrose and acid catalyst be uniformly mixed at the molecular level. Also provided are food products containing these materials.

In further satisfaction of the foregoing objects and advantages, the present invention provides novel products resulting from the polymerization of amorphous sucrose in the presence of an acid catalyst such as citric acid, tartaric acid or phosphoric acid. In this aspect of the invention, there is produced a novel amorphous sucrose acid melt intermediate and polymers characterized herein as fructoglucans, said polymers being produced by the reaction of amorphous sucrose and the acid catalyst at a temperature in the range of 125°-170° C. Also provided are food products containing these novel materials.

BRIEF DESCRIPTION OF THE DRAWINGS

Reference is now made to the drawings accompanying the invention wherein.

DESCRIPTION OF THE PREFERRED EMBODIMENTS

The present invention relates to a series of novel products resulting from the thermolysis of amorphous sucrose under the conditions described herein. These products are sweetener compositions and are especially useful as low calorie sweetener compositions and as bulking agents. These sweetener compositions are also useful as nutritional supplements.

The present invention is concerned with the production of two different groups of products by the thermolysis of amorphous sucrose under selected conditions for each reaction. In one aspect, kestose containing fructose moieties are produced by the reaction of amorphous sucrose with an acid catalyst at temperatures in the range of 80°–110° C. The products resulting from this reaction include several novel products as well as certain known products such as 1-kestose and 6-kestose. In a second major aspect of the invention, amorphous sucrose is polymerized in admixture with an acid catalyst at temperatures of 125°–175° C. to produce a fructoglucan polymer. In either case, the resulting products are useful as nutritional supplements and provide a series of new products resulting from sucrose technology which have not been known heretofore.

In this invention, the starting material, amorphous sucrose, is to be distinguished from conventional crystalline sucrose. The key to the present invention is the use of dried amorphous sucrose as the essential reactant. Amorphous sucrose is defined herein as a sugar having the chemical structure of sucrose and substantially no crystalline X-ray diffraction pattern. The amorphous sucrose is produced from crystalline sucrose according to the method of Lowary et al. supra. In this invention, however, the crystalline sucrose is initially dissolved in water with an acid catalyst. On drying, the product produced is a melt of amorphous sucrose and acid catalyst.

According to the present invention, crystalline sucrose is mixed with an acid catalyst for reaction. The amount of catalyst employed ranges from about 0.2 wt % to 5.0 wt % based on the amount of sucrose. It is preferred that about 1.0 wt % of acid catalyst be combined with the sucrose for best results. The acid catalyst is preferably a food grade acid, or acid salt or acidic buffer. Suitable acids include organic acids which contain one or more characteristic carboxylic acid groups, (and optionally, an hydroxyl group), such as citric acid, tartaric acid, benzoic acid or lactic acid. Inorganic acids such as phosphoric acid may also be used, as well as salts and buffers thereof, including disodium or potassium hydrogen phosphate and sodium or dipotassium dihydrogen phosphate. These materials are referred to herein generally as "acid catalysts". The acid catalyst is preferably non-volatile. Because of the minimum color obtained in the resulting products, citric acid is an especially preferred reactant. Any "acid catalyst" which reacts in the process to produce the products indicated are considered to be within the scope of the invention.

The chemical formula of the starting sucrose and the products produced in accordance with the low temperature aspect of the invention may be described by the following general formula:

(a) Sucrose, $R_1=R_2=R_3=H$;
(b) 1-kestose, $R_1=\beta$-D-fructofuranosyl, $R_2=R_3=H$;
(c) Iso-1-kestose, $R_1=\alpha$-D-fructofuranosyl, $R_2=R_3=H$;
(d) 6-kestose, $R_2=\beta$-D-fructofuranosyl, $R_1=R_3=H$;
(e) Iso-6-kestose, $R_2=\beta$-D-fructofuranosyl, $R_1=R_3=H$;
(f) Neokestose, $R_3=\beta$-D-fructofuranosyl, $R_1=R_2=H$;
(g) Iso-neokestose, $R_3=\alpha$-D-fructofuranosyl, $R_1=R_2=H$.

Of the above compounds, sucrose is of course, the starting material and 1-kestose (b), 6-kestose (d) and neokestose (f) are known compounds in the art. Compounds (c), (e) and (g) are novel compounds.

In conducting the reaction, crystalline sucrose is initially dissolved in water, preferably deionized water, together with the acid catalyst to obtain solution and good mixing of the materials. A minimum amount of water should be used since it must be removed prior to thermolysis. The water is then removed by evaporation using a vacuum at low temperatures. Any suitable method for obtaining admixture of the sucrose and acid catalyst may be utilized, the only critical aspect being that uniform admixture be obtained prior to conducting the reaction. When the water is removed, there is produced an anhydrous melt intermediate, which is amorphous. The obtained mixture of amorphous sucrose and acid catalyst (Anhydrous Melt Intermediate) is believed to represent a novel product which is useful as a nutritional sweetener as well as being an intermediate to produce other useful products as described herein.

After obtaining the amorphous sucrose-acid catalyst anhydrous melt, the mix is subjected to thermolysis under low temperature procedures or high temperature procedures as described herein to produce the products of the invention. Different products are produced depending on the temperature of thermolysis.

Low Temperature Products

The use of lower reaction temperatures results in a series of oligosaccharide products, some of which are known compounds such as 6-kestose and neokestose. The other products produced are novel products.

In conducting the low temperature reaction, the anhydrous sucrose melt is heated at the indicated temperature range of 80°-110° C. until the yield of trisaccharides is maximized. The resulting product is a brittle, amorphous solid, usually pale beige in color. Longer reaction times may cause a darkening in color of the product. At this stage, the useful products can be recovered by one or more of three different procedures. In one procedure, the product is subjected to preliminary fractionation by adding a precipitant, such as a ketone (e.g., acetone) or a lower alkyl ($C_1$–$C_5$) alcohol. In this procedure, preferential precipitation is obtained whereby the kestoses precipitate from unreacted sucrose and glucose.

In a second purification procedure, the kestoses may be purified by use of liquid chromatography or membrane purification using methods known to the art.

In a third procedure, the product can be treated with yeast to ferment unchanged sucrose by fermentation. The yeast is then removed which leaves kestoses which are resistant to attack by yeast. An immobilized enzyme system could also be used.

The products of the sucrose thermolysis at the lower temperatures were expected to include kestose containing fructose moieties linked at C-2 and C-6 and also at C-2 and C-1. Application of the conventional methylation analysis (viz, methylation, hydrolysis, reduction, and acetylation) would not permit the gel liquid chromatography (g.l.c) separation of the trimethyl derivatives resulting from these two linkage types although borodeutride reduction would differentiate the mass spectra. A more discriminating method of analysis was then used. It was known that partially methylated and then acetylated aldoses (Dutton, *Adv. Carbohyr. Chem. and Biochem.*, 30, 1976, p. 9–110), and kestoses (Lindberg et al *Act. Chem. Scand*, 27(5), 1973, p. 1819–1821) can be well resolved despite the problems of anomerization and that they give mass spectra which are readily distinguishable. This type of approach (viz, methylation, hydrolysis, acetylation) was applied to structural analysis of the kestoses. The products were identified by g.l.c./m.s. comparison with authentic standards, the origins of which are indicated in Table I and where the compounds are referred to by numbers 1, 2, 3, 4, 5, 6 and 7. G.l.c. retention times and partial mass spectra of these standards are shown respectively in Tables II and III. The fragmentation patterns of 1 and 4 have already been discussed and the mass spectrum of 3 is readily explainable in the context of previously published material (DeJongh et al., *Jour. Am. Chem. Soc.*, 85, (1963), p. 2289-2294, and Kochetkov, et al. *Adv. Carbohyr. Chem.*, 21, (1966), p. 39–93).

The mass spectra of the furanoside derivatives have not previously been discussed directly, but peaks at m/z 159, 101 and 129 in compounds 2 and 5 and m/z. 187 and 129 in compound 6 are consistent with a fragmentation pattern proposed by Karady and Pines, *Tetrahedron*, 26, (1970), p. 4527–4536, for trimethylsilyl ethers of ketofuranosides. Kochetkov and Chizov, *Tetrahedron*, 21 (1965), p. 2029–2047, have proposed fragmentation pathways for methylfuranosides which could account for the formation of ions 103, 88, 101 and also 146 and 115 from 2 and 6 and the corresponding ions 174 (not observed), 143 and 115 from 5. The propensity of furanoside rings to undergo sequential elimination rather than major fragmentation of the ring has been noted previously, Karady et al, supra, and in accordance with this, peaks at m.z 191, 145 and 113 in 2 and 6 are consistent with successive eliminations of the C-1 with its substituent, the acetoxyl of C-2 as ketene, C-6 with its substituent and methanol. The corresponding peaks in 5 are at m/z 219, 145 and 113.

TABLE I

REFERENCE COMOUNDS FOR METHYLATION ANALYSIS

| Compound | Source |
|---|---|
| 2,3,4,6-tetra-$\underline{O}$-methyl-D-glucose acetate (1) | methyl α-D-glucopyranoside |
| 1,3,4,6-tetra-$\underline{O}$-methyl-D-fructose acetate (2) | methyl β-D-fructofuranoside |
| 2,3,4-tri-$\underline{O}$-methyl-D-glucose diacetate (3) | dextran |
| 2,3,6-tri-$\underline{O}$-methyl-D-glucose diacetate (4) | amylose |
| 1,3,4-tri-$\underline{O}$-methyl-D-fructose diacetate (5) | 6'-$\underline{O}$-tritylsucrose |
| 3,4,6-tri-$\underline{O}$-methyl-D-fructose diacetate (6) | 1-kestose |
| 6-acetyl-1,2,3,4,5-penta-$\underline{O}$-methyl-D-glucitol (7) | isomaititol |

TABLE II

GAS CHROMATOGRAPHY OF PARTIALLY METHYLATED ACETYLATED SUGARS

| Compound[a] | | Approximate Relative Peak Areas | Relative Retention Time ($R_T$) |
|---|---|---|---|
| (2) | PEAK 1 | 1 | 1.00 |
|  | PEAK 2 | 15 | 1.09 |
| (1) | PEAK 1 | 2 | 1.08 |
|  | PEAK 2 | 1 | 1.22 |
| (3) | PEAK 1 | 1 | 2.61 |
|  | PEAK 2 | 1 | 2.82 |
| (4) | PEAK 1 | 6 | 3.29 |
|  | PEAK 2 | 1 | 3.57 |
| (5)[b] |  |  | 2.79 |
| (6)[b] |  |  | 3.19 |
| (7)[b] |  |  | 1.21 |

[a]Numbered as Table I.
[b]Only one g.l.c. peak.

TABLE III

PARTIAL MASS SPECTRA OF REFERENCE COMPOUNDS FOR METHYLATION ANALYSIS

| Reference Compound[a] (m/z) | 1 | 2 | 3 | 4 | 5 | 6 |
|---|---|---|---|---|---|---|
| 69 | 1 | 5 | 3 | 4 | 55 | 3 |
| 71 | 10 | 24 | 7 | 21 | 86 | 12 |
| 73 | 6 | 10 | 8 | 12 | 17 | 12 |
| 75 | 8 | 10 | 16 | 14 | 25 | 6 |
| 87 | 6 | 22 | 14 | 100 | 54 | 24 |
| 88 | 23 | 7 | 25 | 40 | 21 | 6 |
| 89 | 5 | 47 | 3 | 3 | 26 | 16 |
| 99 | 2 | 8 | 4 | 18 | 71 | 6 |
| 101 | 100 | 100 | 100 | 25 | 100 | 100 |
| 102 | 6 | 5 | 4 | 2 | 7 | 6 |
| 103 | 1 | — | 1 | 5 | 43 | 3 |
| 113 | 1 | 2 | 3 | 12 | 10 | 2 |
| 115 | 6 | 12 | 8 | 10 | 10 | 3 |
| 127 | 3 | 5 | 6 | 25 | 13 | 6 |
| 129 | 2 | — | 8 | 80 | 5 | 2 |
| 145 | 1 | 20 | 1 | 2 | 1 | 9 |
| 146 | — | 2 | — | — | — | 2 |
| 159 | 1 | 20 | — | 5 | 17 | 1 |
| 187 | 5 | — | — | 5 | Tr | 18 |
| 191 | — | 22 | — | — | 1 | 1 |

TABLE III-continued

PARTIAL MASS SPECTRA OF REFERENCE COMPOUNDS FOR METHYLATION ANALYSIS

| Reference Compound[a] (m/z) | 1 | 2 | 3 | 4 | 5 | 6 |
|---|---|---|---|---|---|---|
| 218 | — | 3 | — | — | — | — |
| 219 | — | — | — | 1 | 25 | — |
| 233 | — | — | — | 4 | — | — |
| 246 | — | — | — | — | 3 | — |
| 247 | — | — | 3 | 3 | — | — |

[a]Numbered as Table I.

When pure crystalline sucrose is heated, it remains relatively stable until melting at ca. 187° C., whereupon the disappearance of sucrose occurs rapidly, e.g., 88% reacts in 12 minutes at 190° C. The thermolysis of pure sucrose can be observed at much lower temperatures in the absence of crystallinity. Hence, amorphous sucrose was used herein and was found to be generated by rapid evaporation at room temperature of a concentrated aqueous solution. The thermolysis has been conclusively shown to be acid catalyzed in methyl sulfoxide solution and hence a small amount of acid catalyst was included in the preparation of the amorphous sucrose, thereby ensuring also a uniform distribution of the catalyst in the acid-sucrose melts. The choice of acid catalyst was influenced by the high level of acid sensitivity of the sucrose glycosidic linkage and by the requirement that the catalyst be nonvolatile at likely reaction temperatures. Citric acid was selected for the detailed studies. This acid gave products which were much less colored than some alternative catalysts (e.g., tartaric acid and phophoric acid), for reasons which are not known with certainty, but which may involve interception of free radical intermediates in color (caramel) formation by the tertiary C—H group.

The thermal degradations of the acid-sucrose melts in this aspect were carried out under vacuum in a heated oil bath. The vacuum probably does not significantly influence the thermolysis reactions but it ensures the rapid removal of the last traces of water during heat-up to reaction temperature. Obviously, any water allowed to remain in the melt would very rapidly be incorporated by hydrolysis with attendant loss of sucrose. The first step in the acid-catalyzed thermolysis of sucrose is the formation of the resonance stabilized fructofuranosyl cation and glucose, wherein the former then reacts relatively efficiently with the oxygen nucleophiles of the primary alcohol groups of unreacted sucrose to generate kestoses. It was anticipated that the fructosyl cation would react with equal facility with the primary hydroxyl of product glucose.

Figure 1:
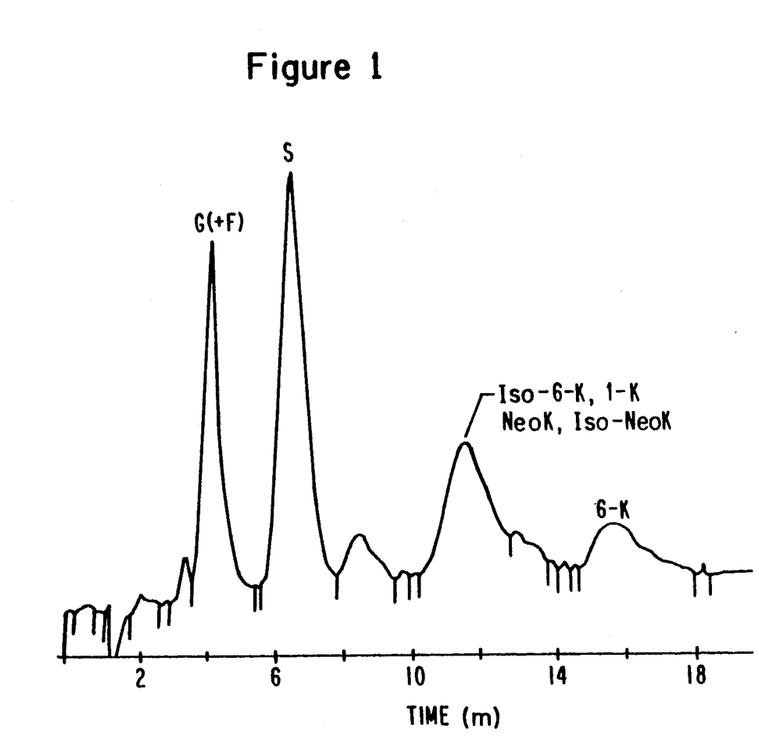
FIGS. 1 and 2 are liquid chromatography fractionation profiles of products from acid-sucrose melts of the invention.
Figure 2:
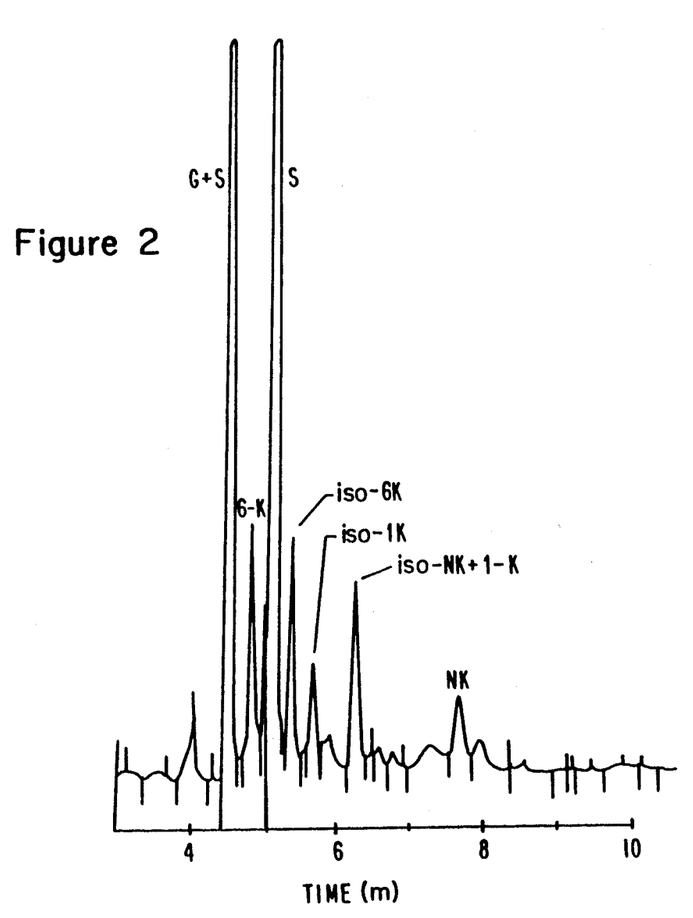

The products of heating the anhydrous sucrose melts (100° C./60 m) were subjected to a preliminary fractional precipitation which separated much of the glucose and some of the unreacted sucrose. The precipitated oligosaccharide products were then fractioned by two successive liquid chromatography procedures, viz, system (a) and then (b). The liquid chromatography profiles given by the total precipitated products in each system are shown in FIGS. 1 and 2.

The four major products isolated by this procedure, included two known compounds, viz, 6-kestose and neokestose. These were identified by liquid chromatographic comparison with authentic compounds and the structures confirmed by methylation, hydrolysis, acetylation and g.l.c./m.s. (Table IV). The third pure compound thus isolated proved to be an α-fructosylsucrose anomer of 6-kestose which was accorded the trivial name of iso-6-kestose (Tables IV and V). The remaining products ran concurrently with 1-kestose on both liquid chromatographic systems; however, methylation analysis revealed, in addition to the expected products derived from 1-kestose, a larger amount of products which would be expected to arise from neokestose. This was confirmed by $^{13}$C nmr (Table VI) which indicated a preponderance of iso-neokestose (α-fructosylsucrose anomer of neokestose) with some 1-kestose. A second work-up procedure involving pretreatment with invertase before precipitation (FIG. 3) yielded three products amenable to isolation by liquid chromatography (system b). One of these was iso-6-kestose. The second was a reducing disaccharide containing fructose and glucose $^1$H and $^{13}$C nmr and borodeutride reduction followed by methylation analysis indicated that this product was 6-α-D-fructofuranosyl-D-glucopyranose (Tables IV and V). A small amount of this compound was detected by liquid chromatography in the original mixture (FIG. 2), but it was greatly augmented by the enzyme treatment, doubtless by the partial hydrolysis of isoneokestose. The presence of this compound among the products of sucrose thermolysis at 170° C. had previously been tentatively deduced. Bollmann et al, supra. The final product obtained from the invertase pre-treatment was iso-1-kestose (α-fructosylsucrose anomer of 1-kestose) (Tables IV and V).

TABLE IV

METHYLATION ANALYSIS OF PRODUCTS OF SUCROSE THERMOLYSIS

| Compound | Products of methylation analysis |
|---|---|
| 6-kestose | 1, 2, 5 |
| Iso-6-kestose | 1, 2, 5 |
| Neokestose | 2, 3 |
| Iso-1-kestose | 1, 2, 6 |
| 1-kestose | 1, 2, 3, 6 |
| Iso-neokestose | 1, 2, 3, 6 |
| 6-α-D-fructofuranosyl-D-glucopyranose | 2, 7(1-$^2$H) |

TABLE V

ASSIGNMENTS OF $^{13}$ C.N.M.R. SPECTRA OF NEW OLIGOSACCHARIDES[a] IN D$_2$O

| Carbon[a] Atom | 1-Kestose | Iso-1-Kestose | 6-α-Fructosyl-D-glucose | | Iso-6-kestose |
|---|---|---|---|---|---|
| | | | β | α | |
| 1' | 62.2 | 62.0 | | | 62.1 |
| 1" | 61.7 | 59.7 | 59.3 | 59.3 | 59.2 |
| 2' | 104.9 | 104.2 | | | 104.5 |
| 2" | 104.5 | 108.9 | 109.2 | 109.0 | 109.2 |
| 3' | 77.9 | 77.1 | | | 76.9 |
| 3" | 77.9 | 81.7 | 81.1 | 81.3 | 80.5 |
| 4' | 75.1 | 74.5 | | | 75.1 |
| 4" | 75.7 | 77.8 | 78.2 | 78.2 | 78.2 |
| 5' | 82.4 | 82.2 | | | 81.0 |
| 5" | 82.4 | 83.9 | (84.2, 84.0) | | 84.2 |
| 6' | 63.5 | 62.9 | | | 63.3 |
| 6" | 63.4 | 61.4 | 61.0 | 61.0 | 62.1 |
| 1 | 93.7 | 93.3 | 96.8 | 93.0 | 92.8 |
| 2 | 72.4 | 71.9 | 74.9 | 72.2 | 71.9 |
| 3 | 73.8 | 73.4 | 76.6 | 73.7 | 73.4 |
| 4 | 70.5 | 70.0 | 70.6 | 71.0 | 70.2 |
| 5 | 73.6 | 73.2 | 75.3 | 75.3 | 73.1 |
| 6 | 61.4 | 60.9 | 62.0 | 62.0 | 61.3 |

[a]Double primed numbers refer to the fructose unit appended to sucrose in the kestoses and to glucose in the disaccharide.
[b]Dominant anomer.

TABLE VI

CHEMICAL SHIFTS OBSERVED IN THE SPECTRA OF A MIXTURE OF ISO-NEOKESTOSE AND 1-KESTOSE IN $D_2O$ WITH TENTATIVE ASSIGNMENTS

| Chemical Shift | 1-Kestose | Iso-neokestose |
|---|---|---|
| 108.8 | | 2'' |
| 104.5 | 2' | 2' |
| 104.0 | 2'' | |
| 93.3 | 1 | |
| 92.9 | | 1 |
| 83.4 | | 5'' |
| 82.1, 82.0, 81.5 | 5, 5'' | 5' |
| 77.7 | | 4'' |
| 77.4, 77.2 | 3', 3'' | 3' |
| 75.3 | 4'' | |
| 74.9, 74.6 | 4' | 4' |
| 73.4 | 3 | 3 |
| 73.2 | 5 | |
| 72.1 | | 2 |
| 71.9 | 2 | |
| 71.8 | | 5 |
| 70.3 | | 4 |
| 70.0 | 4 | |
| 63.4, 63.1, 63.0 | 6', 6'' | 6' |
| 62.1 | | 6'' |
| 61.9, 61.7 | 1' | 6 |
| 61.2 | | 1' |
| 60.9 | 6 | |
| 60.7, 59.8 | 1'' | 1'' |

Figure 4:
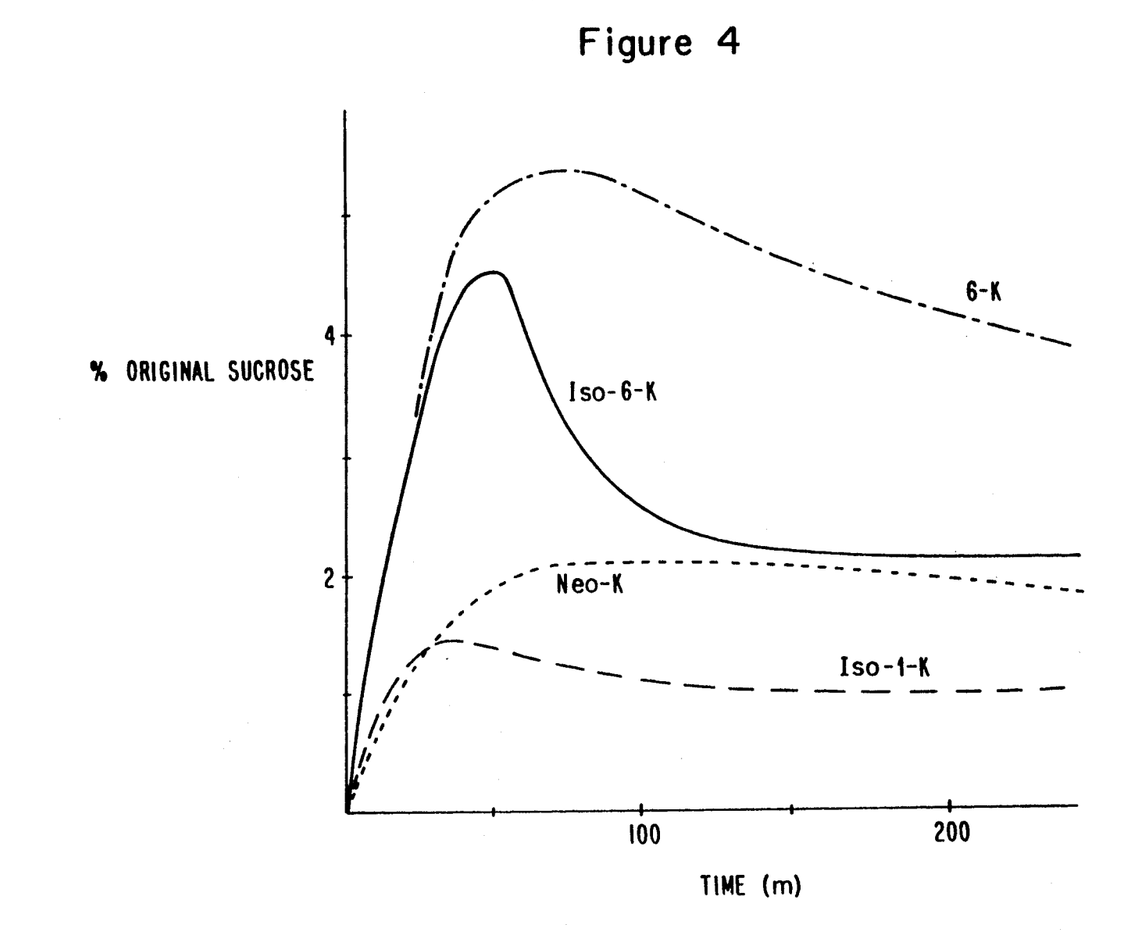
FIG. 4 is a graph illustrating yields of kestoses from a 1% citric acid-sucrose melt.

When pure samples of the kestose products were available, it was possible to determine their liquid chromatographic response factors. The progressive contents of four of the kestose products in the acid-sucrose melts at 100° C. were then determined by liquid chromatography (method [b]) and are shown in FIG. 4. Iso-6-kestose forms rapidly to reach a maximum at ca.1 hour and then decreases, presumably by undergoing thermolysis to form either fructosyl cation and sucrose or a difructosyl cation and glucose. 6-kestose forms at a similar rate, but is less rapidly degraded, perhaps suggesting that the α-fructofuranosyl linkage undergoes thermolysis more rapidly than the comparable β-fructofuranosyl linkage. It was not possible to confirm this by comparison of the other two isomeric pairs since iso-neokestose and 1-kestose are concurrent under the liquid chromatographic system used. The combined curve for these two is not shown in FIG. 4, but was similar in form and magnitude to that for iso-6-kestose. The lower yield of iso-1-kestose is reminiscent of the general lower reactivity of the 1'-hydroxyl of sucrose in selective derivatization.

The relative reactivities of the kestose to invertase have been determined with yeast invertase (β-D-fructofuranosidase) and are shown in Table VII in comparison with sucrose. The presence of an α-D-fructofuranosyl group at either of the primary positions of the fructose residue would be expected to confer complete immunity to attack by a β-fructofuranosidase and this is borne out by the isolation of unchanged iso-1-kestose and iso-6-kestose after drastic invertase pre-treatment of the oligosaccharide products from sucrose thermolysis. Iso-neokestose, on the other hand, has an exposed β-fructofuranosyl residue and although the α-linked fructosyl at C-6 of the glucose moiety confers immunity to the conditions used in this experiment (Table VII), under more drastic enzyme pre-treatment iso-neokestose was degraded to 6-α-fructosylglucose.

TABLE VII

ACTION OF INVERTASE (β-D-FRUCTOFURANOSIDASE) ON KESTOSES

| Substrate | $t_{0.5}(m)$ |
|---|---|
| Sucrose | <<0.5 |
| 1-Kestose | 3.5 |
| 6-kestose | 1.2 |
| Neokestose | 3.8 |
| Iso-1-kestose | No reaction detected up to 24 h. |
| Iso-6-kestose | No reaction detected up to 20 h. |
| Iso-neokestose[a] | No reaction detected up to 20 h. |

[a] Actually measured on iso-neokestose contaminated with a small amount of 1-kestose, which degraded relatively rapidly.

HIGH TEMPERATURE PRODUCTS

In a further aspect of the invention, the amorphous sucrose-acid catalyst melt is reacted in the indicated amounts at higher temperatures, i.e., temperatures in the range of 125°–175° C., for a period ranging from about eighty minutes up to two days. It has been found, however, that at longer heating periods an acceptable polymer is still produced, but the color may be darker. In this reaction as in the lower temperature reaction, sucrose is first formed into the anhydrous acid sucrose melt by dissolving in a minimal amount of water and then evaporating the water rapidly at a low temperature as described.

After heating at the selected higher temperature is completed, the product is cooled and at this stage has the appearance of a "taffy" material in that it is a brittle, amorphous, brownish solid. As noted above, the longer the heating period occurs, the darker will be the color.

This material is processed first by fractionating by initially dissolving in water to precipitate the polymer by addition of an appropriate amount of a lower alkyl alcohol (e.g., ethanol) such as about 40–60 wt %. The product precipitates from solution as a solid precipitate which can be recovered by a separation means such as a centrifuge.

The material remaining in solution comprises glucose oligosaccharides and fructose oligosaccharides as well as glucose-fructose oligosaccharides. There are also present in the solution difructose dianhydrides. These compounds may be recovered from the solution by evaporation of the liquid. These oligosaccharides are produced during the high temperature thermolysis in yields of about 60%. These oligosaccharides materials are useful as nutritional aids to influence favorable microflora in the lower digestive tract and as animal food nutrients.

In conducting the initial thermolysis reaction, higher temperatures require shorter periods for formation of the polymer. In general, lower temperatures for longer times appear more desirable for producing less color. Longer heating times provided higher yields of total polymer but more color. At both temperatures, there was a significant increase in proportion of the high molecular weight fraction with increasing time as indicated by gel permeation chromatography. In a comparison of air versus vacuum for polymerization at 125° C. and 140° C., there was a small increase in the proportion of high molecular weight product using vacuum. Replacement of air by Argon for the polymerization at 140° C. had an insignificant effect. It should be noted that all water should be removed from the acid-sucrose melt before heating, otherwise hydrolysis rather than polymerization may occur. Removal of this water will require use of a vacuum normally.

It is known that the commercial product polydextrose may be produced from glucose by a treatment similar to that described herein for sucrose. A major difference, however, is that a crystalline mixture of glucose and citric acid (plus some glucitol) is used whereas it is essential in the process of this invention that amorphous (non-crystalline) sucrose be used. The advantages of the polymers produced from sucrose as described here is that they contain fructose as well as glucose and hence, have very different properties from polydextrose. In the mechanism for polymerization of sucrose, glucose may be produced as an intermediate product, together with fructosyl cation and fructose-sucrose oligosaccharides. The formation of total polymer is more rapid with glucose than with sucrose, although the rate of formation of the high molecular weight polymer is similar. In the present work, it will be noted that an amorphous acid/glucose melt was used for comparison with the sucrose system whereas in commercial polydextrose preparation it is generally believed that a crystalline mixture of glucose and citric acid should be used which probably requires higher temperatures for polymerization. Fructose alone does not polymerize rapidly probably because the dominant pyranose form is slower to produce the required cation. A mixture of glucose and fructose yielded more polymer than does sucrose. The former product, however, is more colored and probably contains a large proportion of glucan without fructose, i.e., polydextrose.

The polymer recovered from this reaction is a novel polysaccharide namely, a fructoglucan. This is a highly branched material similar to polydextrose but is a distinct and novel material. For example, there is no fructose in glucose polymers whereas both glucose and fructose occur in the fructoglucan polymers. The molecular weight of the polymer produced according to the present invention ranges from 2,000 to 10,000 Dalton and has an average of 20 sugar units. The polymer may be characterized as having a glucose to fructose ratio of 1.3:1 up to 2:1, preferably 1.3:1 up to 1.7:1 with a preferred average ratio of 1.66:1.

The fructoglucan polymer of this invention is useful as a sweetener and as a bulking agent, for example, which is a utility similar to the polydextrose products. However, the fructoglucan of the present invention has an advantage over the polydextrose products in having a better mouth feel and taste.

All the products of the invention are useful as human and animal food additives, e.g., as sweetener additives, especially low calorie additives, nutritional supplements, and as bulking agents. When used, the products are added to foods in amounts ranging from abut 0.01 wt. % up to 25 wt. %. The kestoses appear especially useful as health food additives for humans and animals (e.g., chickens and pigs). The oligosaccharides produced with the fructoglucan are different from the kestoses, but are also food additives.

The following examples are presented to illustrate the invention, but it is not considered to be limited thereto. In the examples, and elsewhere in this specification, the parts are by weight unless otherwise indicated.

EXAMPLE I

In the following examples liquid chromatography was carried out using (a) Waters μ-Bondapak $NH_2$, 8 mm×10 cm, 10 μmm Radial-Park cartridge column with acetonitrile: water (30:20) at 4 mL/minutes; or (b) Waters Resolve $C_{18}$, 8 mm×10 cm, 5 μm Radial-Pak cartridge column with water at 1 mL/minute and a Waters differential refractometer R401. Separation of the product mixture into its components was achieved by successive preparative liquid chromatography through (a) and then (b) after the method of Ivin and Clarke, *J. Chromatog.*, 408 (1987), p. 393-398. Optical rotations and some nmr spectra were measured by T. Lowary at the University of Edmonton. Molecular weights and formulae were determined by f.a.b./m.s. carried out by J. Sears at Montana State University. Authentic kestoses were a gift from M. A. Clarke and W. S. C. Tsang of Sugar Producers Research Institute, New Orleans, La..

Methylation Analysis of Oligosaccharide Products

Methylations were carried out following the method of Ciucanu and Kerek, *Carbohydr. Res.*, 131 (1984), p. 209-217. Samples (0.5-2 mg) were dissolved in methylsulfoxide (0.5 mL) with stirring in a capped vial, the solution was cooled to ca. 10° C. and finely powdered sodium hydroxyde (20-30 mg) added followed after 10-15 minutes by methyl iodide (200 μL). The resulting mixture was stirred at 10° C. for 45 minutes, then excess methyl iodide removed in a stream of dry air. Water (1.0 mL) and chloroform (1.0 mL) were added and mixed, the upper layer discarded, the chloroform layer washed with water (3×1.0 mL) and finally evaporated under a stream of dry air.

Methylated fructofuranosides and kestoses were hydrolyzed with 90% acetic acid (100 μL) at 100° C. for 10 minutes in a sealed vial followed by the addition of water (500 μL) and further heating at 100° C. for 60 minutes. In the case of methylated glucopyranosides the acetic acid was replaced with trifluroacetic acid. Acetylation of dried hydrolysis products was carried out in dry pyridine (100 μL) and acetic anhydride (100 μL) at 25° C. overnight, prior to g.l.c./m.s. which was carried out using a Hewlett-Packard 5890A gas chromatograph fitted with a Supelco SP 2330 fused silica capillary column (30 m×0.2 mm I.D.) connected via capillary direct interface with a Hewlett-Packard 5970 series mass selective detector, ionizing potential 70 cV. G.l.c. temperature was 180° C. isothermal.

Thermal Degradation of Sucrose and Isolation of Products

Powdered sucrose (Baker analyzed reagent; 6.0000 g) was dissolved in deionized water (4.0 mL) together with citric acid (0.0600 g). The water was then mostly removed (80-85 wt %) at room temperature under 0.1 mm Hg, leaving a solid sponge of amorphous sucrose. The sample was heated in an oil bath (1000°±0.1° C.) under the same vacuum for 60 minutes. Within 10-15 minutes, the solid sponge had collapsed to a viscous liquid which on eventual cooling, hardened to a transparent pale yellow-brown glass. This was dissolved in water (30 mL) and absolute ethanol (30 mL) added. Acetone (220 mL) was then added dropwise with stirring until a white precipitate formed, which on standing settled as an oily deposit from which the clear supernatant was decanted. The precipitate was dried under vacuum, then dissolved in water for preparative liquid chromatography.

Figure 3:
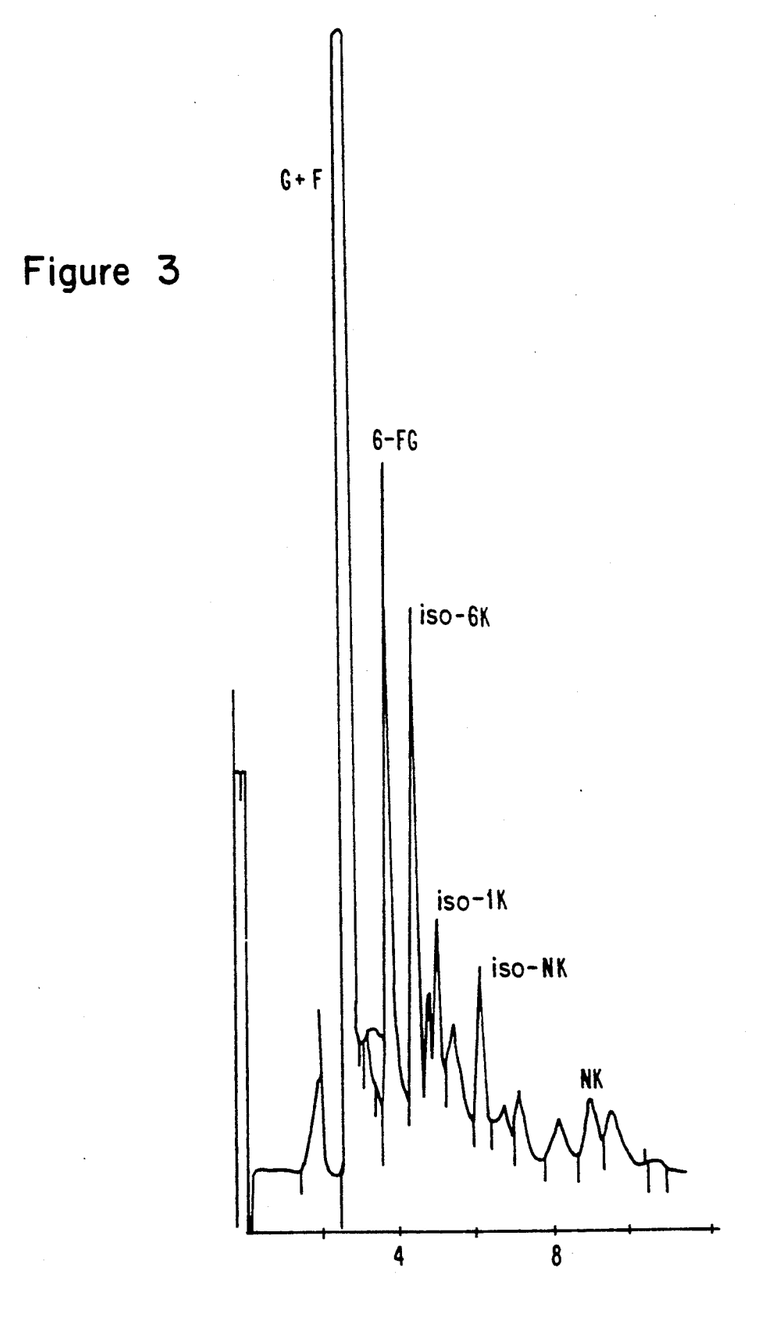
FIG. 3 is a liquid chromatographic profile of a product mixture after invertase treatment but before precipitation.

A similar sample of the precipitate (4 g) was dissolved in water (15.0 mL), solid yeast invertase (Sigma, 825 units/mg; 6.3 mg) added and the sample incubated at 37° C. After 30 minutes, the oligosaccharides were precipitated as previously described using ethanol (15.0 mL) and acetone (240 mL). Liquid chromatography (system b) of this product revealed that all of the sucrose and most of the product oligomers had been degraded to glucose and fructose (FIG. 3). There remained two components apparently resistant to invertase and a new substance had formed (6-FG in FIG. 3).

Identification of Products of Thermal Degradation

From the precipitate which had not been treated with invertase, four components were isolated as amorphous solids by liquid chromatography. Two of these gave single peaks when co-injected with authentic samples of 6-kestose and neokestose, respectively on both liquid chromatographic systems. Methylation analysis was consistent with these assignments (Table IV). Of the remaining two products, one was not coincident in liquid chromatography with any known kestose. Methylation analysis (Table IV) showed this substance to be isometric with 6-kestose. $^{13}$C nmr (Table V) indicated the presence of an α-linked fructofuranoside. Subsequently this product was shown to be one of the invertase-resistant components. On the basis of this evidence it was named iso-6-kestose (f.a.b./m.s. M+1=505.181 6. Calc. for $C_{18}H_{33}O_{16}$505.1800), $[\alpha]+40.5°$ (cl, $D_2O$). Methylation analysis and $^{13}$C nmr of the final component indicated that it was a mixture of 1-kestose and an isomer of neokestose, which were coincident on both liquid chromatographic systems. F.a.b./m.s. of the mixture (M+1=505.1803) was consistent with this conclusion. Treatment of this mixture with invertase and examination by liquid chromatography showed the formation of glucose and fructose, together with the same new substance observed from the total product mixture after enzyme treatment. This new substance (5 mg) was isolated by liquid chromatography as an amorphous solid and reduced in aqueous solution (0.25 mL) with sodium borodeutride (5 mg in 0.25 mL). The reaction mixture was acidified by shaking with Amberlite resin IRC 50 (H) (1 mL), filtered and blown dry repeatedly with methanol (6×1 mL) at 25° C. The reduced product was then subjected to methylation analysis which gave 1,3,4,5-tetra-Q-methyl-D-fructose diacetate and 6-acetyl-1,2,3,4,5-penta-Q-methyl-D-(1-$^2$H)glucitol. The mass spectrum of the latter compound is not included in Table III because of its structural dissimilarity from the other reference compounds. The major fragment ions were 101 (100%), 117 (53), 90 (30), 75 (26), 102 (24), 60 (19), 161 (16), 146 (16), 88 (16), 87 (13). $^1$H nmr ($D_2O$) revealed that a doublet (J=3.7 Hz) at 5.20 ppm (C-1α) and another doublet (J=7 9 Hz) at 4.63 ppm (C-1α). These integrated in the ratio 1:1.56. $^{13}$C nmr ($D_2O$) (Table V) was also consistent with an equilibrium mixture of glucose anomers to which the fructofuranosyl moiety is α-linked;

$$[\alpha]\frac{22}{D} + 57.6 \, (cl, D_2O).$$

The methylation analysis shows that the fructose is linked to the 6-position of glucose. Since the 1-kestose in the original two component mixture would be degraded completely by invertase (Table VII) this reducing disaccharide must result from the other trisaccharide which is liquid chromatographically coincident with 1-kestose. This other component was therefore identified as iso-neokestose.

The invertase treatment of the oligosaccharide thermolysis products was stated above to yield three products after liquid chromatographic separation. Of these, one proved to be iso-6-kestose and one, the 6-Q-(α-D-fructofuranosyl)-D-glucose arising from iso-neokestose. The third component isolated as an amorphous solid, $$[\alpha]\frac{22}{D} + 62.2° \, (cl, D_2O),$$

on methylation analysis proved to be isometric with 1-kestose. $^{13}$C nmr (Table V) indicated an α-linked fructoranoside moiety. This product was therefore named iso-1-kestose.

Relative Rates of Formation of Kestoses

Small samples (ca. 70 mg) of amorphous sucrose containing 1% citric acid were heated under vacuum in an oil bath (100±0.1° C.) for varying times. Kestose products were determined from integrated liquid chromatographic peak areas by comparison with an external standard of sucrose using the following relative response factors previously determined with pure compounds: 6-kestose, 0.64; neokestose, 0.71; iso-1-kestose, 0.92.

Reaction of Kestoses with β-fructofuranosidase

Kestose solutions (200 μL; ca. 10 mg/mL) were incubated with yeast invertase (Sigma; 50 μL; 2700 units/mL) at 37° C. The rate of disappearance of kestose was monitored by liquid chromatography and is reported in Table VII.

EXAMPLE 2

In this example, a series of experiments were carried out for production of the sucrose polysaccharide of this invention. In this example, the influence of temperature, the effective time of heating, the atmosphere for polymerization, and alternative work-up procedures were investigated. In all of the following experiments, the initial anhydrous melt was prepared as described in Example 1 and the same ratios of reactants were employed. The only differences are as set forth in this example.

In studies on the influence of temperature, it was found that higher temperatures require shorter times for formation of the polymer. In general, however, lower temperatures for longer times appear to produce less color and a high proportion of the high molecular weight component.

At temperatures of 125° and 170° C., the lower and higher temperature limits, longer heating times provided higher yields of total polymer but more color. At both temperatures, there was a significant increase in proportion of high molecular weight fraction with increasing time. The experiments with respect to the influence of temperature are shown in the following Table VIII and the effective time of heating on yield is shown in Table IX below.

With respect to the atmosphere for polymerization, in a comparison of air versus vacuum for polymerization at 125° C. and 140° C., there was a small increase in the proportion of high molecular weight product in vacuum. Replacement of air by argon for the polymerization at 140° C. had an insignificant effect. It was noted during these experiments that all water must be removed from the anhydrous melt before heating takes place or otherwise hydrolysis rather than polymerization may occur. Removal of water, therefore, will require vacuum. These distinctions are shown in Table X.

For a comparison of the sucrose polysaccharides resulting from this invention with glucose and fructose thermal polymers known to the art, the commercial product polydextrose was produced from glucose by treatments similar to that described herein for sucrose. The major difference is that a crystalline mixture of glucose and citric acid (plus some glucitol) is used whereas with sucrose, it is essential that anhydrous or non-crystalline sucrose be used. The expected advantage of the polymers from the sucrose of this invention is that they should contain fructose as well as glucose and hence, have very different properties from polydextrose. In the mechanism for polymerization of sucrose, it was postulated that glucose would be an intermediate product together with a fructosyl cation and fructose-sucrose oligosaccharides. Therefore, in Table XI, the behavior of glucose and fructose under the conditions used for sucrose polymerization were studied and Table XI shows a comparison using reprecipitation to isolate the high molecular weight product.

TABLE VIII

Effect of Temperature on Yield

| Temperature | Time | Conditions | Raw Yield | Total Yield After Dialysis |
|---|---|---|---|---|
| 125 | 6 hrs | air | 9.6% | 3.76% |
| 140 | 3 hrs | air | 18% | 5% |
| 155 | 1 hr | air | 18% | 6.75% |
| 170 | 50 min | air | 24.8% | ND |

TABLE IX

Effect of Time on Yield

| Temperature | Time | Conditions | Raw Yield | Total Yield After Dialysis |
|---|---|---|---|---|
| 125 | 6 hrs | air | 9.6% | 3.76% |
| 125 | 9 hrs | air | 15% | 5.65% |
| 125 | 18 hrs | air | 19.9% | 9.78% |
| 125 | 30.5 hrs | air | 31.8% | 15.3% |
| 125 | 46 hrs | air | 38% | 25% |
| 170 | 20 min | air | 7.7% | ND |
| 170 | 50 min | air | 24.8% | ND |
| 170 | 100 min | air | 37% | ND |

TABLE X

Effect of Atmospheric Conditions on Yield

| Temperature | Time | Conditions | Raw Yield | Total Yield After Dialysis |
|---|---|---|---|---|
| 125 | 46 hrs | air$^a$ | 36.1% | 17% |
| 125 | 46 hrs | vacuum$^a$ | 39% | 25.6% |
| 140 | 3 hrs | air$^b$ | 18% | 5% |
| 140 | 3 hrs | argon$^a$ | 14% | 6% |
| 140 | 3 hrs | vacuum$^a$ | 19% | 9.5% |

$^a$Reactions carried out in side-arm conical flask with walls considerably thicker than the usual reaction vessel.
$^b$Carried out in usual reaction vessel.

TABLE XI

Comparison of Sucrose Polymers with Glucose, Fructose and Glucose/Fructose polymers

| Type | Temperature | Time (Hr) | Conditions | Raw Yield | Total Yield After Dialysis |
|---|---|---|---|---|---|
| Sucrose | 125 | 30.5 | air | 31.8% | 15.3% |
| Glucose | 125 | 30 | air | 80.9% | 21.9% |
| Fructose | 125 | 30 | air | 7.9% | 5.5% |
| Glucose and Fructose | 125 | 30 | air | 36.1% | 20.8% |

The formation of total polymer is more rapid with glucose than with sucrose, although the rate of formation of high molecular weight polymer is similar. In these experiments, it should be noted that an amorphous acid/glucose melt was used for better comparison with the sucrose system whereas in commercial polydextrose preparation, it is believed that a crystalline mixture of glucose and citric acid is used which probably requires higher temperatures for polymerization. Fructose alone does not polymerize rapidly, probably because the dominant pyranose form is slower to produce the required cation. A mixture of glucose and fructose yielded rather more polymer product than did sucrose. The former product, however, was more colored and appeared to contain a large proportion of glucan without fructose, i.e., polydextrose.

The molecular weights of the products were determined by gel permeation chromatography as a method of choice. The gel permeation chromatography systems used Sephadex gels, refractive index detection, and computer processing of data with the system being calibrated with oligosaccharide and polysaccharide standards.

The compositional analysis of the polymeric products indicates that there is significant glucose and fructose content. There appears to be three types of chromofluor in their products with maxima at 224, 282 and 348. There is also a lower level of caramel type continuous adsorption at higher wave lengths which is responsible for the visible color.

Molecular Weight Studies on the Sucrose Polysaccharide (Fructoglucan)

Figure 5:
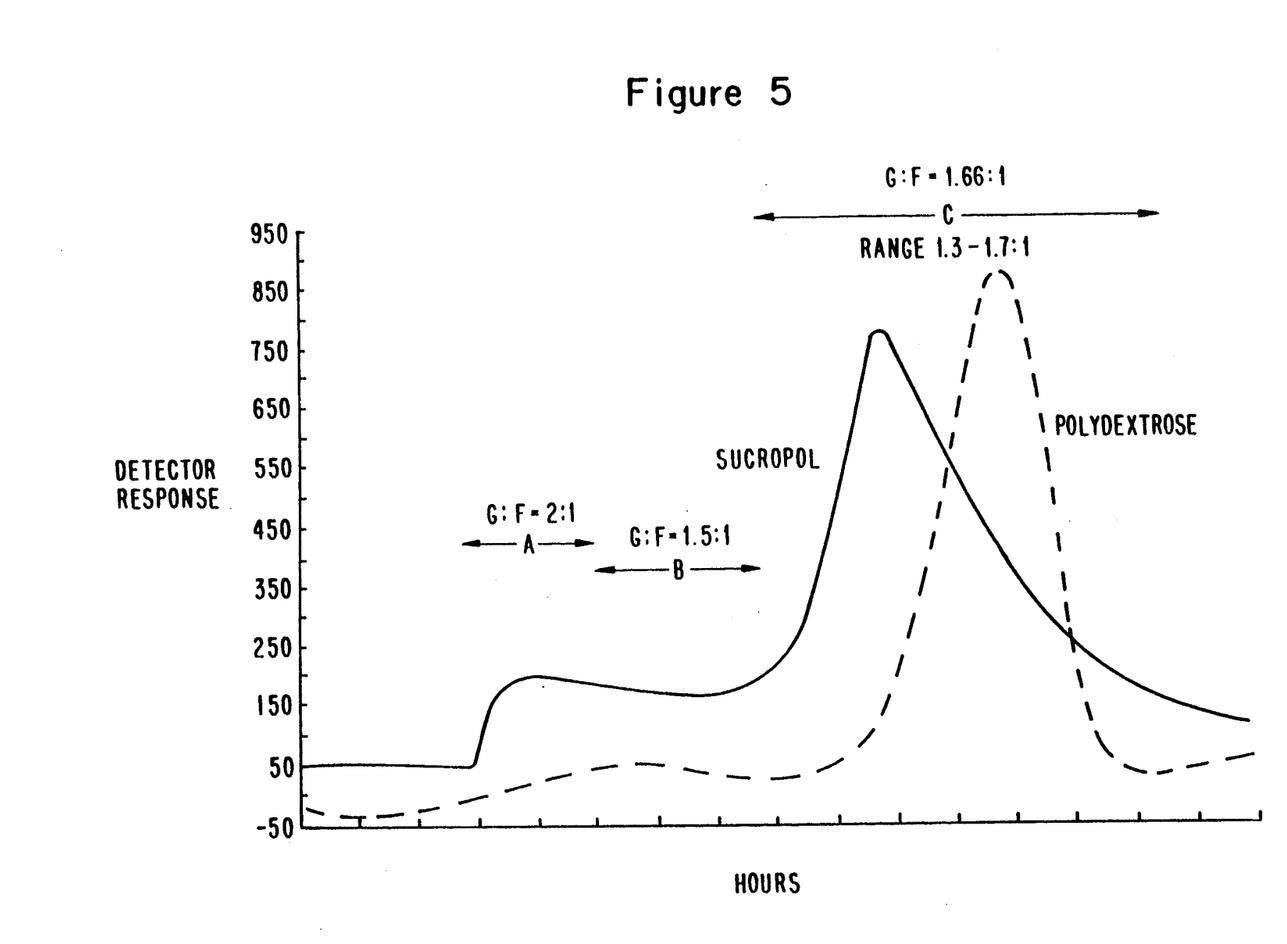
FIG. 5 is a gel permeation chromatographic graph of differential refractive index comparing the fructoglucan of this invention with polydextrose and malto oligosaccharides.
Figure 6:
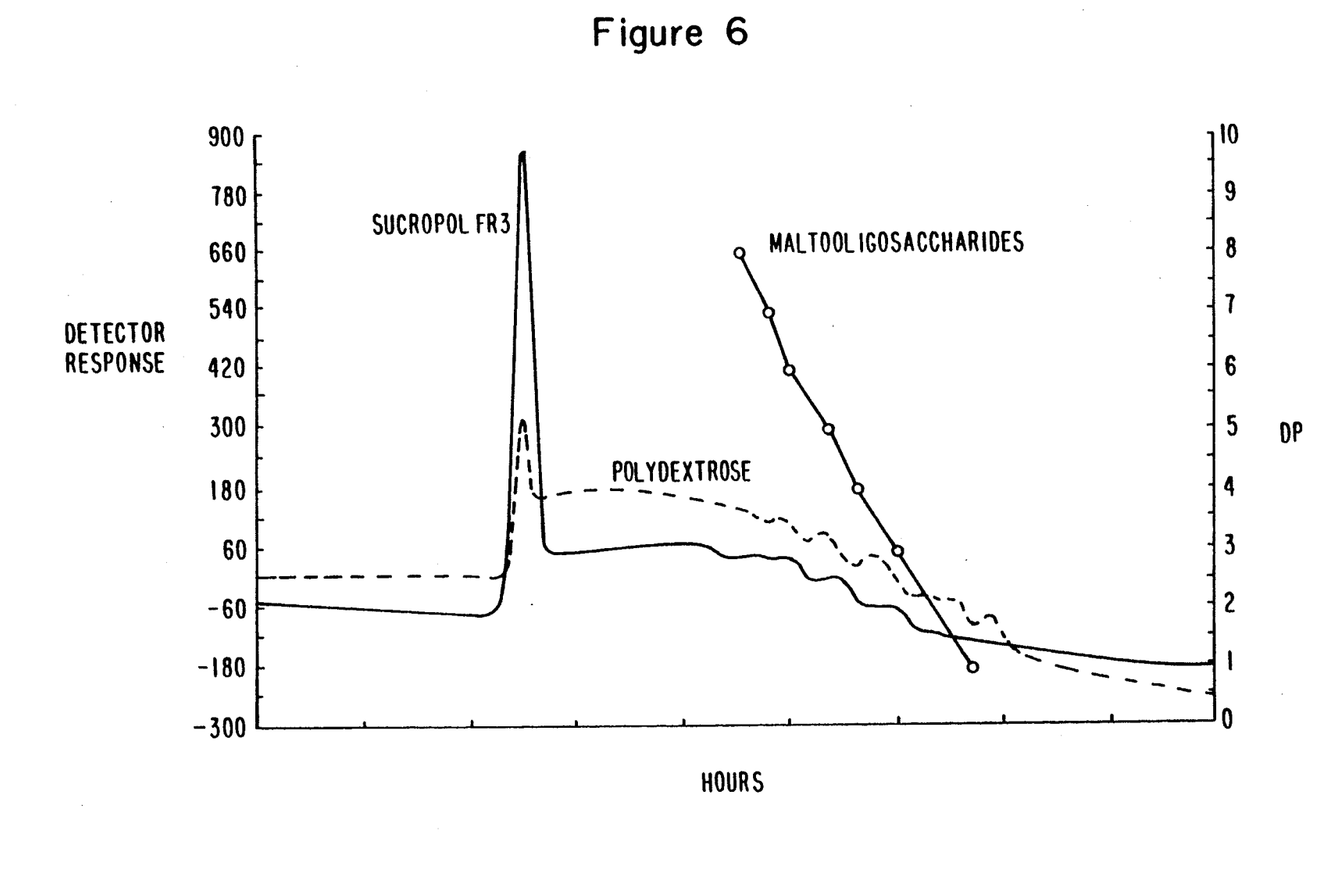
FIG. 6 is a gel permeation chromatography profile by Sephadex G-100 comparing the fructoglucan of this invention with polydextrose.

Gel permeation chromatography (g.p.c.) was used with two different gel porosities and detection by differential refractive index. The gel profile given by Sephadex G100 is shown in FIG. 5. This gel excludes polysaccharides greater than d.p. ca. 600 and fractionates polysaccharides of d.p. ca. 5-600. All of the visible color in the fructoglucan is concentrated in the high molecular weight ($V_o$) peak A. Most of the mass of the product is in Peak The peak C (i.e., the mass of the fructoglucan) evidently has a slightly higher molecular weight range than commercial polydextrose. It is reasonable to assume that this component of the sucrose fructoglucan would have similar food bulking properties to polydextrose. Refractionation of peak C on Biogel P2 is shown in FIG. 6. The elution volumes for a series of maltodextrins are shown in the same Figure. These dextrins cannot be used for unequivocal calibration of the fructoglucan because the latter will certainly involve a very wide range of linkage types and will also contain fructose as well as glucose. However, FIG. 6 suggests that the fructoglucan has an average molecular weight greater than d.p. 10 and also confirms that it contains a significant larger proportion of higher molecular weight material than polydextrose.

The patent and commercial literature regarding polydextrose suggests that some glucitol is deliberately included with glucose in the polymerization. There was similarly included 10% glucitol in some of the sucrose polymerizations here. In these experiments, no significant effect was detected in the general molecular weight distribution. However, there was significant amplification of the g.p.c. profile in the di-/tri-saccharide region. This may indicate formation of a fructosyl glucitol and is being further investigated.

Compositional Analysis of the Fructoglucan

There is extreme difficulty in compositional analysis of the fructoglucans. Such polymers have not previously been isolated (apart from some natural fructans carrying a sucrose end group). In the polymer here, it was assumed that both furanose and pyranose linkages are present and both glucose and fructose units are present within the polymer chain. Therefore, hydrolytic conditions adequate to hydrolyze fructopyranosyl and glucopyranosyl linkages were used. These conditions cause significant degradation of fructose after hydrolysis; therefore any conventional approach to compositional analysis was ruled out.

Figure 7:
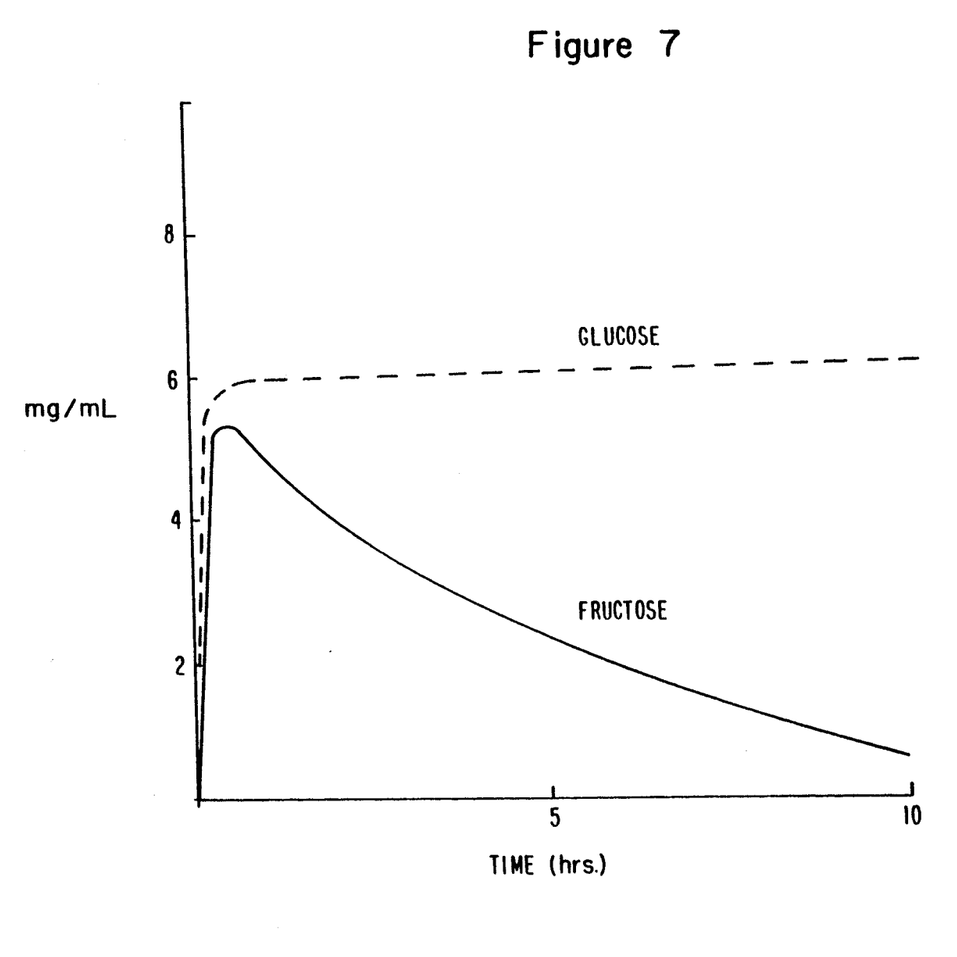
FIG. 7 is a graph showing the decomposition of fructose (derived from sucrose) under conditions adequate for pyranoside hydrolysis.

One way to resolve this problem involved calibrating the rate of acid decomposition of fructose (derived from sucrose) under conditions adequate for pyranoside hydrolysis (e.g., 1M trifluoracetic acid at 100° C. for 5 hours). It was shown that these conditions produce no significant degradation of glucose after hydrolysis, but that fructose is degraded to about 24% of its original value (FIG. 7). The precision in these measurements is relatively low, but they provided a procedure to acid hydrolyse the fructoglucan, analyze glucose and fructose by liquid chromatography, correct for degradation of fructose and thus obtain an approximate ratio of glucose to fructose in the fructoglucan. The ratio by this method was approximately G:F=2:1. It was evident, however, that a more reliable method was required for the compositional analysis.

The preferred method was developed from a procedure described by Z. Dische (Methods in Carbohydrate Chemistry, 1, 1962, 481) for determination of kestoses. The method involves treatment of part of the sample with cysteine under acid conditions and gives a response for fructose with only minor and measurable interference from glucose. On another sample of the polymer, the total carbohydrate is determined by use of the phenol-sulfuric acid method. The latter method gives a different response for glucose and fructose, respectively, and an algorithm is used to calculate total carbohydrate content using the fructose value from the cysteine method. The method has been tested on glucose, fructose, methyl-$\beta$-D-fructopyranoside, turanose, palatinose and the fructoglucan. These reference compounds include glucopyranoside and fructopyranoside linkages and hence are a suitable series with which to test for complete hydrolysis of the fructoglucan. The fructose-containing standards all gave a response by the cysteine method of about 6.1 absorption units per micromole, except for palatinose, which gave a slightly higher response. The glucose response by the cysteine method was 0.03 absorption units per micromole, i.e., a 211-fold sensitivity difference. The derived fructose yields confirmed that complete hydrolysis had been effected. The response of the fructoglucan, when related to its phenol-sulfuric acid response, indicated that the polymer was comprised of 32% fructosyl residues.

The invention has been described herein with reference to certain preferred embodiments. However, as obvious variations thereon will become apparent to those skilled in the art, the invention is not to be considered as limited thereto.

What is claimed is:

1. A compound selected from the group consisting of iso-1-kestose, iso-neokestose, iso-6-kestose, 6-[$\alpha$-D-fructofuranosyl]-D-glucose, and mixtures thereof.

2. A compound according to claim 1 which is iso-6-kestose.

3. A compound according to claim 1 which is iso-neokestose.

4. A compound according to claim 1 which is iso-1-kestose.

5. A compound according to claim 1 which is 6-[$\alpha$-D-fructofuranosyl]-D-glucose.

6. Anhydrous amorphous sucrose melt product which is the dried product of amorphous sucrose and about 0.2 to 5 wt % of an acid catalyst.

7. A product according to claim 6 wherein the acid catalyst is selected from the group consisting of organic acids, inorganic acids, acidic buffers and acid salts.

8. A product according to claim 7 wherein the acid catalyst is selected from the group consisting of citric acid, tartaric acid, benzoic acid, lactic acid, disodium or dipotassium hydrogen phosphate, sodium or potassium dihydrogen phosphate, phosphoric acid and phosphate buffers.

9. A mixture of products produced by the thermolysis of amorphous sucrose said mixture containing 1-kestose, 6-kestose, neokestose, iso-1-kestose, iso-6-kestose, and iso-neokestose.

10. A product according to claim 6 wherein the anhydrous melt is prepared by dissolving sucrose and acidic catalyst in water to obtain solution, and then removing the water to produce the anhydrous sucrose melt.

11. A fructoglucan polymer produced by the reaction of sucrose and an acidic catalyst, said fructoglucan polymer having a molecular weight of about 2,000 to 10,000 Daltons and containing a ratio of glucose units to fructose units of about 1.3:1 up to 2:1.

12. A polymer according to claim 10 which is produced by reaction of sucrose and an acidic catalyst to form an anhydrous melt, then heating said anhydrous melt at a temperature of 125°–175° C.

13. A mixture of oligosaccharides produced by the reaction of sucrose and an acidic catalyst to form an anhydrous melt, then heating said anhydrous melt at a temperature of 125°–175° C.

14. A method for the preparation of a compound of claim 13 which comprises heating a mixture of sucrose and an acid catalyst at a temperature from about 80°–110° C.

15. A method according to claim 14 wherein the sucrose and acid catalyst are initially contacted in water to form a mixture, the water is removed to form an anhydrous sucrose melt, then said melt is subjected to heating at temperatures of about 125° to 175° C. for up to two days.

16. A method according to claim 15 wherein about 0.2 to 5 wt. % of acid catalyst is reacted with said sucrose.

17. A method for the preparation of a compound of claim 1 which comprises heating a mixture of sucrose and an acid catalyst at a temperature from about 80°–110° C.

18. A method according to claim 17 wherein sucrose and acid catalyst are initially contacted in water to form a mixture, the water is removed to form an anhydrous sucrose melt, then said melt is subjected to heating at temperatures of 80°–110° C.

19. A method according to claim 17, wherein about 0.2 to 5 wt % of said acid catalyst is reacted with said sucrose.

20. A method according to claim 18 wherein the acid catalyst is selected from the group consisting of organic acids, inorganic acids, acidic buffers, and acid salts.

21. A method according to claim 20 wherein the acid catalyst is selected from the group consisting of citric acid, tartaric acid, benzoic acid, lactic acid, disodium or dipotassium hydrogen phosphate, sodium or potassium dihydrogen phosphate, phosphoric acid, phosphate buffers, and mixtures thereof.

22. A method for the preparation of a polymer of claim 11 which comprises heating a mixture of sucrose and an acid catalyst at a temperature from about 125°–175° C.

23. A method according to claim 22 wherein sucrose and acid catalyst are initially contacted in water to form a mixture, the water is removed to form an anhydrous sucrose melt, then said melt is subjected to heating at temperatures of about 125° to 175° C. for up to two days.

24. A method according to claim 23 wherein about 0.2 to 5 wt % of acid catalyst is reacted with said sucrose.

25. A method according to claim 24 wherein the acid catalyst is selected from the group consisting of organic acids, inorganic acids, acidic buffers and acid salts.

26. A method according to claim 23 wherein the acid catalyst is selected from the group consisting of citric acid, tartaric acid, benzoic acid, lactic acid, disodium or dipotassium hydrogen phosphate, sodium or potassium dihydrogen phosphate, phosphoric acid and phosphate buffers, and mixtures thereof.

27. A sweetener composition comprising a compound of claim 1 and a carrier.

28. A sweetener composition containing a compound of claim 6 and a carrier.

29. A sweetener composition containing the mixture of claim 9 and a carrier.

30. A sweetener composition containing a polymer of claim 11 and a carrier.

31. A composition comprising a food and a compound of claim 1.

32. A composition comprising a food and a compound of claim 6.

33. A composition comprising a food and the mixture of claim 9.

34. A composition comprising a food and a fructoglucan polymer of claim 11.

35. A composition of claim 31 wherein the food is an animal food.

36. A composition of claim 32 wherein the food is an animal food.

37. A composition of claim 33 wherein the food is an animal food.

38. A composition comprising an animal food and the mixture of claim 13.

* * * * *